United States Patent [19]

Magnusson et al.

[11] Patent Number: 5,280,427
[45] Date of Patent: Jan. 18, 1994

[54] PUNCTURE GUIDE FOR COMPUTER TOMOGRAPHY

[75] Inventors: Anders Magnusson; Dan Åkerfeldt, both of Uppsala, Sweden

[73] Assignee: Bard International, Inc., Murray Hill, N.J.

[21] Appl. No.: 618,298

[22] Filed: Nov. 27, 1990

[30] Foreign Application Priority Data

| Nov. 27, 1989 | [SE] | Sweden | 8904006 |
| Mar. 12, 1990 | [SE] | Sweden | 9000876 |
| Mar. 12, 1990 | [SE] | Sweden | 9000877 |
| Mar. 12, 1990 | [SE] | Sweden | 9000878 |
| Mar. 12, 1990 | [SE] | Sweden | 9000879 |

[51] Int. Cl.$^5$ ............................................. G06F 15/00
[52] U.S. Cl. ............................... 364/413.01; 128/754; 606/130
[58] Field of Search ............ 364/413.01, 413.02, 364/413.13; 128/754, 749, 760; 606/167, 130

[56] References Cited

U.S. PATENT DOCUMENTS

| 3,589,361 | 6/1971 | Loper | 128/214.4 |
| 4,058,114 | 11/1977 | Soldner | 128/754 |
| 4,249,541 | 2/1981 | Pratt | 128/753 |
| 4,402,324 | 9/1983 | Lindgren et al. | 128/660 |
| 4,465,069 | 8/1984 | Barbier et al. | 128/303 B |
| 4,469,106 | 9/1984 | Harui | 128/662.05 |
| 4,497,325 | 2/1985 | Wedel | 128/754 |
| 4,527,569 | 7/1985 | Kolb | 128/660 |
| 4,583,538 | 4/1986 | Onik et al. | 128/303 B |
| 4,592,352 | 6/1986 | Patil | 128/303 B |
| 4,681,103 | 7/1987 | Boner et al. | 128/303 B |
| 4,686,997 | 8/1987 | Oloff et al. | 128/653 |
| 4,733,661 | 3/1988 | Palestrant | 128/DIG. 26 |
| 4,735,215 | 4/1988 | Goto et al. | 128/754 |
| 4,791,934 | 12/1988 | Brunnett | 128/653.1 |
| 4,898,178 | 2/1990 | Wedel | 128/662.05 |
| 4,911,173 | 3/1990 | Terwilliger | 128/662.06 |
| 4,944,308 | 7/1990 | Åkerfeldt | 128/754 |
| 4,953,558 | 9/1990 | Åkerfeldt | 606/171 |

FOREIGN PATENT DOCUMENTS

| 8910091 | 11/1989 | Hungary | 128/754 |
| 2094590 | 9/1982 | United Kingdom . | |

OTHER PUBLICATIONS

*Nytt Stereotaktiskt Instrument Underlätar Datortomografiskt Vägledda Punktioner* ("New Stereotactic Instrument Facilitates Computer Tomographically Guided Puncture"), Läkartidningen, vol. 85, No. 21, pp. 1885-1888 (1988).

Primary Examiner—Roy N. Envall, Jr.
Assistant Examiner—Laura Brutman
Attorney, Agent, or Firm—Jones & Askew

[57] ABSTRACT

An apparatus is disclosed for guiding the needle of a tissue sampling device to a target location within the body of a patient. The device permits accurate and easy retrieval of acceptable tissue specimens from locations within the body of a patient which require angling of the needle to reach the target tissue. The apparatus further permits accurate and easy retrieval of tissue specimens from even small pathological changes, and the apparatus can be introduced into the tomograph with the patient to verify correct location of the biopsy needle with respect to the target tissue. The device not only directs the biopsy needle along the desired path but also controls the depth of penetration of the needle to prevent accidental overpenetration of the needle. The guidance device is not limited to the plane normal to the longitudinal axis of the patient but is capable of guiding the needle in a plane which is oblique to the longitudinal axis.

22 Claims, 8 Drawing Sheets

PUNCTURE GUIDE FOR COMPUTER TOMOGRAPHY

TECHNICAL FIELD

The present invention relates generally to an apparatus and method for guiding a biopsy needle to a desired location within a patient's body and relates more specifically to a puncture guide for use in conjunction with computer tomography and method for use thereof.

BACKGROUND OF THE INVENTION

Today ultrasonics, X-ray, computer tomography (also known as "CT scan"), and other imaging technologies are used to visualize and localize pathological changes, e.g. tumors, within a patient's body. X-ray and ultrasonics have limited use in visualizing and localizing such tumors because the body constitution of the patient often hides the suspected pathological change and because small changes cannot be detected. Computer tomography does not have these limitations.

Once a suspected pathological change has been located with a visualization apparatus such as CT scan, it is necessary to retrieve a tissue sample of the suspected tumor for biopsy. Tissue samples are commonly obtained by puncturing the skin of the patient with a biopsy needle, guiding the needle to the site of the suspected tumor, and withdrawing a sample of the tissue. Punctures in the thorax, abdomen and pelvis are conventionally performed by hand after suitable localization of the pathological change. Vertically performed punctures are usually relatively simple to accomplish and provide a relatively high frequency of acceptable tissue specimens, while punctures performed by hand which require an angling of the puncture needle cannot be performed without difficulty and give a lower frequency of successful results. Furthermore, when retrieving tissue samples of small pathological changes, it is very difficult, if not impossible, to hit the target tissue or organ when guiding the needle by hand.

Thus, there is a need for an apparatus which permits accurate and easy retrieval of acceptable tissue specimens from locations within the body of a patient which require angling of the needle to reach the target tissue.

There is a further need for an apparatus which permits accurate and easy retrieval of tissue specimens from small pathological changes.

Various instruments are known for assisting in guiding biopsy needles to a location identified by computer tomography. One such puncture instrument comprises a needle guide which can be angled and is mounted on a stand arranged on the patient table. The stand is vertically and horizontally adjustable relative to the patient table, and the needle guide is either displaceably mounted on the stand or the stand is displaceably mounted to the patient table. Adjustments can be made in x-, y- and z-directions, and the needle guide can be angled 0°-180°. With this instrument, however, repeated attempts are often necessary to obtain an acceptable specimen from the target tissue. Such repeated efforts are time consuming, increase the expense of the procedure, and are painful for the patient in cases where local anesthetic cannot be administered. Furthermore, where multiple attempts are necessary to retrieve a satisfactory tissue sample, additional CT images are required to check needle placement, exposing the patient to further radiation and tying up the CT table for extended periods of time. Also, known prior art guidance devices cannot be brought with the patient into the tomograph to check the position of the needle.

Thus, there is a need for an apparatus which provides increased accuracy of needle placement, thereby reducing the duration of the procedure and minimizing the radiation to which the patient is exposed.

There is also a need for an apparatus which can shorten the time required to retrieve a tissue sample and thereby reduce the expense and discomfort associated with the procedure.

There is a further need for an apparatus which can be introduced into the tomograph with the patient to verify correct location of the biopsy needle with respect to the target tissue.

Yet another disadvantage of known prior art guidance devices is that while such devices are capable of directing the biopsy needle along a desired path, they do not control the location of the needle along that path, that is, the devices do not control the depth of penetration of the biopsy needle. Thus, it is possible for the biopsy needle to be directed along the proper path but for the needle tip to be directed to a location either proximal or distal to the target tissue. Not only can improper penetration depth result in failure to direct the biopsy needle to the target tissue to obtain a tissue specimen, but also accidental overpenetration can result in laceration or perforation of organs or vessels lying distal to the target tissue.

Thus, there is a need for an apparatus which not only directs the biopsy needle along the desired path but also controls the depth of penetration of the needle to prevent accidental overpenetration of the needle.

Still further problems arise with known prior art guidance devices when the skin entry point and the target tissue do not lie in the same axial slice. Known prior art guidance devices are limited to directing the needle in an axial plane, that is, in a plane normal to the longitudinal axis of the patient. Thus, where the optimum needle path lies in a plane which is oblique to the longitudinal axis of the patient, the guidance device cannot be used. The physician must resort to guidance of the biopsy needle by hand, with the attendant problems and disadvantages previously discussed.

Thus, there is a need for a guidance device which is not limited to directing a biopsy needle along a path which lies in a plane normal to the longitudinal axis of the patient.

SUMMARY OF THE INVENTION

Stated generally, the present invention relates to an improved apparatus for guiding a tissue sampling device to a target location within the body of a patient. The apparatus permits accurate and easy retrieval of acceptable tissue specimens from locations within the body of a patient which require angling of the needle to reach the target tissue. The apparatus permits accurate and easy guidance of the biopsy needle to even small pathological changes, and the apparatus can be introduced into the tomograph with the patient to verify correct location of the biopsy needle with respect to the target tissue. The apparatus not only directs the biopsy needle along the desired path but also controls the depth of penetration of the needle to prevent accidental overpenetration of the needle. Furthermore, the guidance device is not limited to directing the needle along a path lying in a plane normal to the longitudinal axis of the patient but is capable of guiding the needle in a plane which is oblique to the longitudinal axis.

Stated somewhat more specifically, the present invention comprises an apparatus for guiding a puncture instrument through an entry point in the body of a patient to a target location within the body of the patient. The apparatus comprises a support means for establishing a fixed reference point adjacent to said body of said patient. A path determining means is mounted to the support means and is adjustable to define a path through the entry point in a predetermined direction. An instrument holding means mounted to the path determining means holds a puncture instrument and moves the puncture instrument along the path defined by the path determining means. A depth determining means operatively associated with the path determining means limits the extent of the movement of the puncture instrument along its path such that the puncture instrument penetrates the patient's body only to a predetermined depth.

In the disclosed embodiment, the puncture guiding apparatus further includes an instrument guide means operatively associated with the path determining means for guiding the puncture instrument as the puncture instrument is moved along the path defined by the path determining means. The instrument guide means of the disclosed embodiment automatically disengages from the puncture instrument when the puncture instrument reaches the limit of its movement. In one embodiment, the instrument guide means comprises a pair of cooperating jaws mounted to the path determining means. The jaws disengage from the puncture instrument when the puncture instrument reaches the limit of its movement. In a more particular embodiment, the pair of cooperating jaws are pivotably mounted to the path determining means for articulation in a horizontal plane. Both of the jaws pivotably disengage from the puncture instrument when the puncture instrument reaches the limit of its movement. In another embodiment, one of the pair of cooperating jaws is pivotably mounted to the path determining means for articulation in a vertical plane. The vertically articulating jaw pivotably disengages from the puncture instrument when the puncture instrument reaches the limit of its movement. Advantageously, the instrument guide means is removably mounted to the path determining means.

In another aspect of the invention, a recoil suppression means is operatively associated with the depth determining means and captures the puncture instrument when the puncture instrument reaches the limit of its movement to prevent the puncture instrument from recoiling.

In yet another aspect of the invention, the patient lies on a support surface. The support means for establishing a fixed reference point adjacent to said body of said patient comprises a track mounted to the support surface. A carriage is movably mounted to the track, and a support arm is mounted to the carriage, with the path determining means being mounted to the support arm. Advantageously, the track comprises a curved upper surface for minimizing artifacts when the puncture guidance apparatus is used in conjunction with imaging technology.

Thus, it is an object of the present invention to provide an improved apparatus for guiding a tissue sampling device to a target location within the body of a patient.

It is another object of the present invention to provide an apparatus which permits accurate and easy retrieval of acceptable tissue specimens from locations within the body of a patient which require angling of the needle to reach the target tissue.

Another object of the present invention is to provide an apparatus which permits accurate and easy retrieval of tissue specimens from even small pathological changes.

Still another object of the present invention is to provide an apparatus which can be introduced into the tomograph with the patient to verify correct location of the biopsy needle with respect to the target tissue.

It is yet another object of the present invention to provide an apparatus which not only directs the biopsy needle along the desired path but also controls the depth of penetration of the needle to prevent accidental overpenetration of the needle.

A further object of the present invention is to provide a guidance device which is not limited to a plane normal to the longitudinal axis of the patient but which can direct a biopsy needle along a path lying in a plane oblique to the longitudinal axis of the patient.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
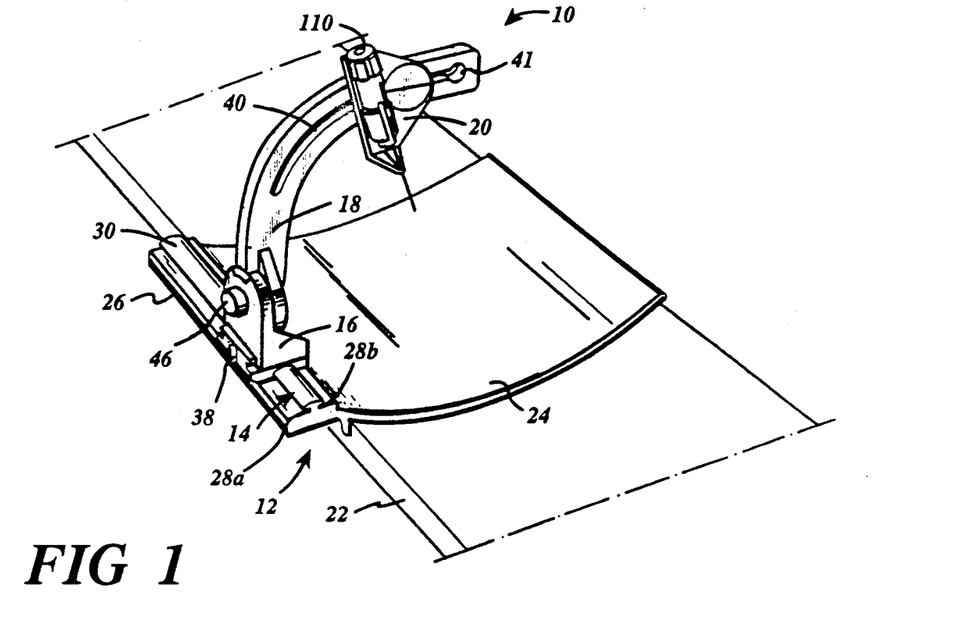
FIG. 1 is a perspective view of a puncture guidance device according to the present invention.

Referring now to the drawings, in which like numerals indicate like elements throughout the several views, FIG. 1 discloses a puncture guidance device 10 according to the present invention. The puncture guide 10 comprises a base 12 having an elongated track 14 thereon, a carriage 16 movable along the track, a support arm 18 mounted to the carriage, and a path determiner 20 movably mounted to the support arm. Each of these components will now be discussed in more detail.

The base 12 is mounted to the patient table 22 of the computer tomograph. The base 12 includes a concave back plate 24 which is disposed generally beneath the portion of the patient from which a tissue specimen is desired. The track 14 runs the length of the base 12 along one lateral edge 26 thereof. The track 14 is generally T-shaped and defines opposing channels 28a, 28b. The upper surface 30 of the track 14 is convex. Preferably the track 14 is comprised of a microcellular polyurethane plastic or other material which exhibits low-attenuation for the used radiation. This plastic is suitable for computer tomography and MNR-tomography.

Figure 2:
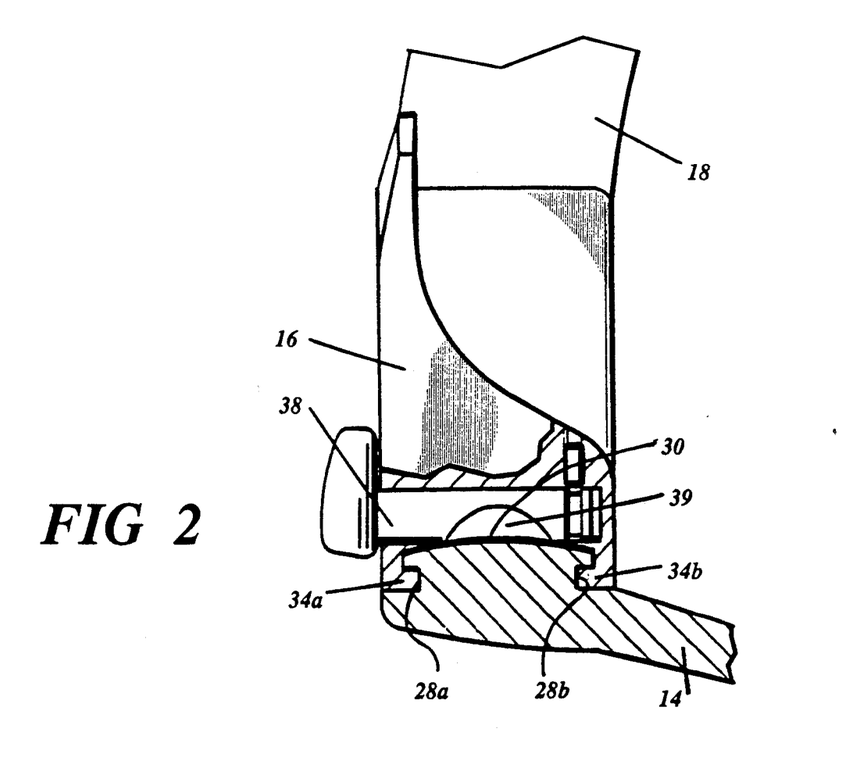
FIG. 2 is a side cutaway view of the carriage and track of the puncture guidance device of FIG. 1.
Figure 3:
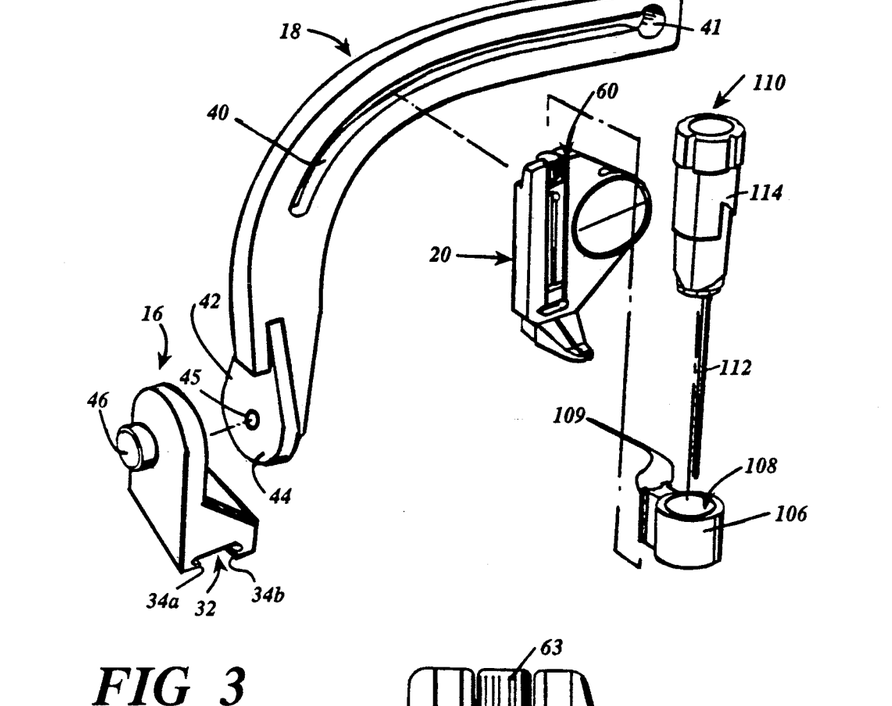
FIG. 3 is an exploded view of the carriage, support arm, path determiner, instrument holder, and puncture instrument of the guidance device of FIG. 1.

As can perhaps best be seen in FIG. 3, the carriage 16 is on its bottom provided with a groove 32 comprising a pair of opposing, mutually facing L-shaped profiles 34a, 34b. Referring again to FIG. 2, the inwardly extending legs of the L-shaped profiles 34a, 34b of the carriage 16 engage the channels 28a, 28b of the track 14 such that the carriage is longitudinally slidable on the track. The carriage 16 further includes a locking pin 38 rotatably mounted within the carriage generally transverse to the direction of elongation of the track 14. The locking pin 38 has a concave recess 39 formed therein conforming generally to the convex curvature of the upper surface 30 of the track 14. When the locking pin 38 is pivoted to rotate the recess 39 into alignment with the upper surface 30 of the track 14, the carriage 16 is freely displaceable along the length of the track. When the locking pin 38 is pivoted to rotate the recess 39 away from the upper surface 30 of the track 14, as depicted in FIG. 2, the shank of the locking pin is brought into interfering engagement with the upper surface of the track and locks the carriage 16 with respect to the track.

Referring now to FIG. 3, the support arm 18 includes a curved body portion having a guide slot 40 formed therein. The guide slot 40 has an enlarged portion 41 at its upper end. The generally rounded lower end 42 of the support arm 18 includes a flattened mounting surface 44 having a threaded bore 45 formed therein. A horizontally extending mounting bolt, the gripping portion of which is designated by the reference numeral 46, is inserted through a smooth bore in the carriage 16 and threadingly engages the bore 45 in the support arm 18. Tightening the bolt draws the mounting surface 44 snugly against the mutually facing portion of the carriage 16. The support arm 18 can thus be pivoted about a horizontal axis to a desired position and retained in that position by tightening the mounting bolt. This mounting arrangement provides the advantage that the support arm 18 is not restricted to a vertical plane but rather can be tightened at an angle with respect to the carriage 16, the advantage of which will become apparent.

Figure 4:
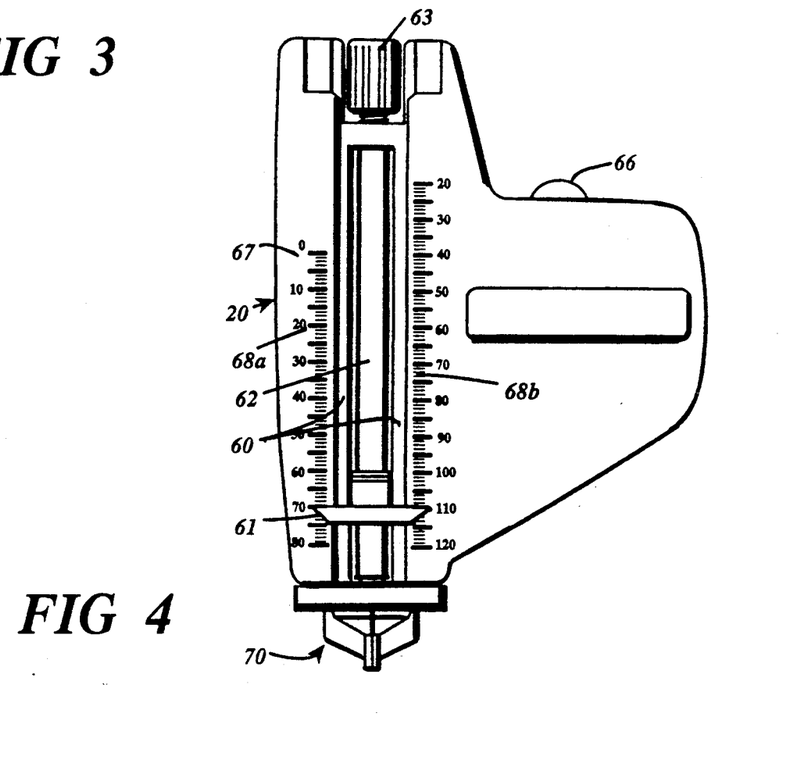
FIG. 4 is a front view of the path determiner of the puncture guidance device of FIG. 1.
Figure 5:
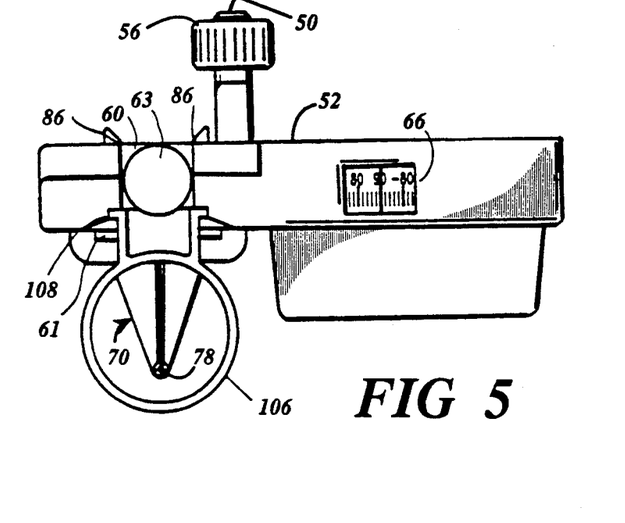
FIG. 5 is a top view of the path determiner of FIG. 4.
Figure 6:
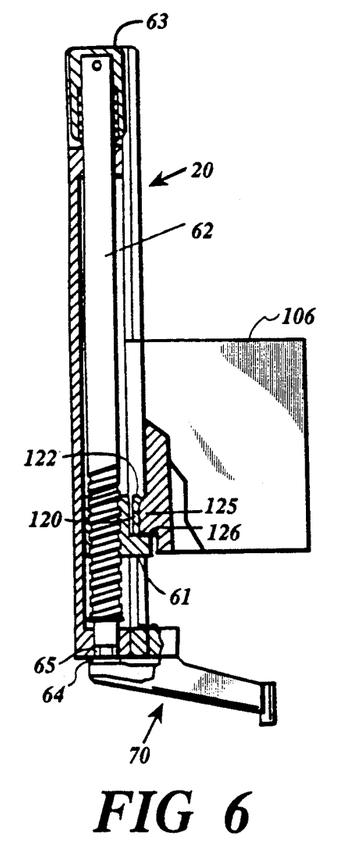
FIG. 6 is a side view of the path determiner of FIG. 4 partially cut away to reveal interior detail.

The construction of the path determiner 20 will now be discussed with reference to FIGS. 4-6. As seen in FIG. 5, a mounting bolt 50 is slidably mounted within a vertical slot in the rear surface 52 of the path determiner 20. A knurled knob 56 is located at the end of the bolt 50. The bolt 50 rides within the guide slot 40 in the support arm 18, and the path determiner 20 can be locked at a given position and angle with respect to the support arm by tightening the knurled knob 56 on the mounting bolt 50. The path determiner 20 is further slidable on the mounting bolt 50 within its vertical slot to permit adjustment of the height of the path determiner with respect to the support arm 18. With reference to FIG. 3, the knob 56 is larger than the major portion of the guide slot 40 and normally prevents the path determiner 20 from becoming disengaged from the support arm 18 when the knob is loosened but still engaged. However, the knob 56 is configured to be able to pass through the enlarged end portion 41 of the guide slot 40. Thus, the path determiner 20 can be quickly attached to and detached from the support arm 18 without having to completely remove the knob 56 from the bolt 50 simply by slightly loosening the knob, sliding the path determiner to the upper end of the slot 40, and then extracting the knob through the enlarged slot portion 41. The path determiner 20 can be mounted to either lateral surface of the support arm 18 and can be easily moved from one side of the support arm to the other if the need should so dictate.

Referring again to FIGS. 4-6, the path determiner 20 has an elongated groove 60 formed therewithin. A shelf 61 is movably disposed within the groove and threadably engages a screw 62 which runs the length of the groove 60. By rotating a knob 63 at the upper end of the screw 62, the screw is turned, the threaded engagement between the screw and the shelf 61 moving the shelf within the groove 60. The height of the shelf 61 with respect to the path determiner 20 can thus be adjusted, for the purpose to be described below. The screw 62 is provided with a limited degree of vertical movement with respect to the path determiner 20 and is normally spring-biased upwardly. At the lower end of the screw is a disc-shaped flange 64, and immediately above the flange is a reduced portion or annular recess 65. The function and purpose of the flange 64 and annular recess 65 will be more fully explained hereinbelow.

The path determiner 20 is further provided with an angle meter 66 for ascertaining the orientation of the path determiner 20 in the support plane in number of degrees relative to the horizontal or vertical planes. The angle meter 66 is of conventional design and functions in the same manner as a water-level. The front surface 67 of the path determiner 20 has a pair of vertical scales 68a, 68b imprinted thereon, one scale on either side of the groove 60, for the purpose to be hereinbelow explained.

Figure 7:
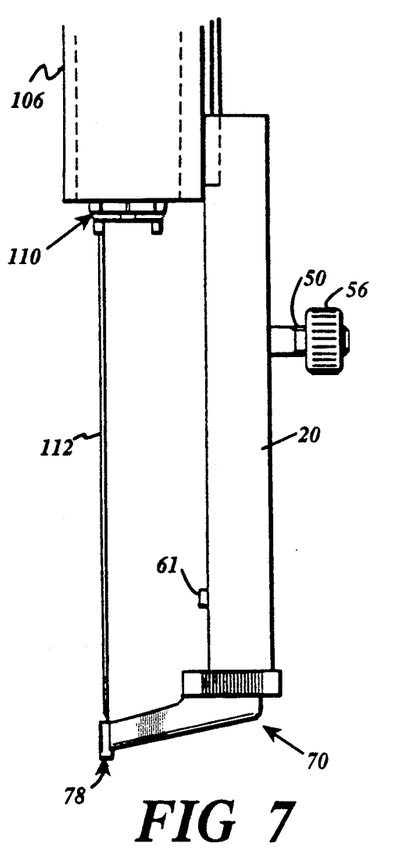
FIG. 7 is a side view of the path determiner of FIG. 4 with a tissue sampling instrument mounted thereto.
Figure 8A:
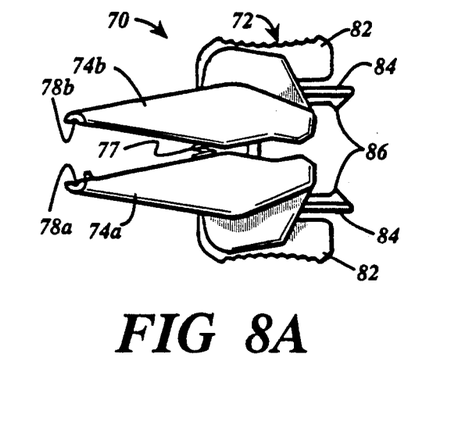
FIG. 8A is a bottom view of a needle guide of the puncture guidance device of FIG. 1 showing the jaws of the needle guide opened.
Figure 8B:
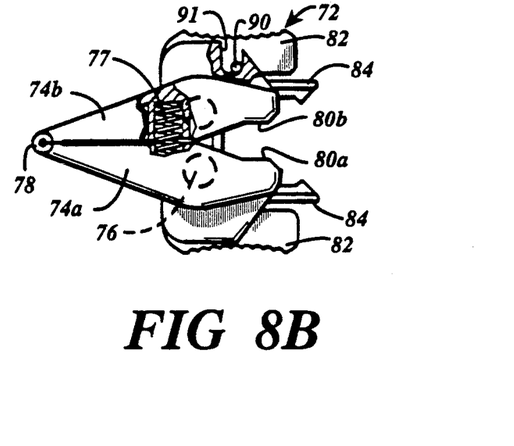
FIG. 8B is a bottom view of the needle guide of FIG. 8A showing the jaws of the needle guide closed.
Figure 8C:
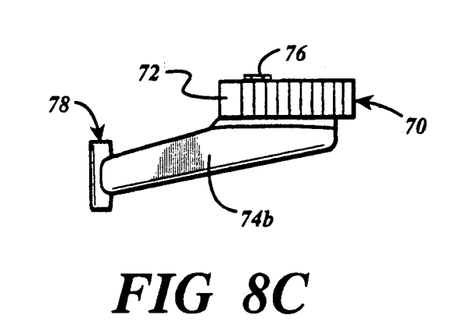
FIG. 8C is a side view of the needle guide of FIG. 8A.
Figure 8D:
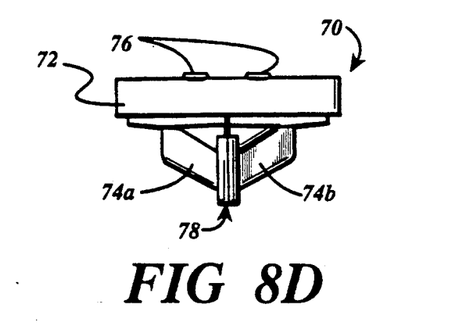
FIG. 8D is a front view of the needle guide of FIG. 8A with the jaws of the needle guide closed.
Figure 8E:
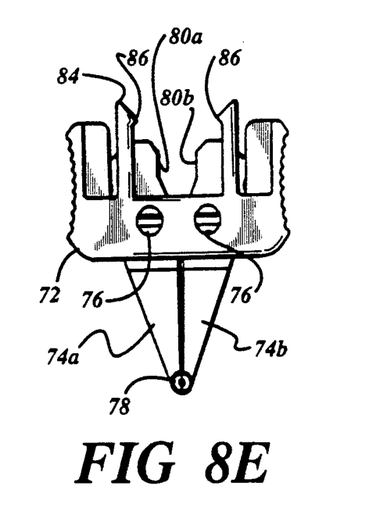
FIG. 8E is a top view of the needle guide of FIG. 8A with the jaws of the needle guide closed.
Figure 9:
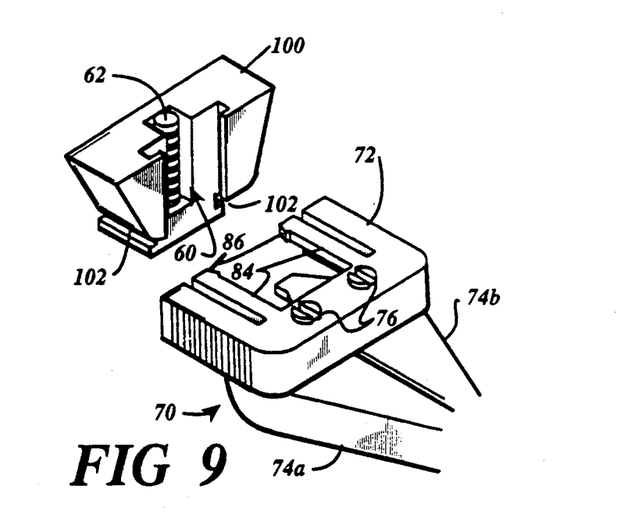
FIG. 9 is a perspective view of the mounting arrangement by which the needle guide is mounted to the path determiner.

Referring now to FIGS. 7–9, a needle guide 70 is mounted to the lower end of the path determiner 20. As can best be seen in FIGS. 4A–E, the needle guide 70 is of primarily plastic construction and comprises a body member 72 and opposing articulating jaws 74a, 74b. Each of the jaws 74a, 74b is pivotably mounted to the needle guide body member 72 by means of a vertical pivot pin 76 so that the jaws articulate in a generally horizontal plane. The jaws 74a, 74b project forwardly from the body member 72 and are biased outwardly by a spring 77. In the forward end of the articulating jaws 74a, 74b are cooperatively aligned semicircular recesses 78a, 78b configured such that when the jaws are closed, the recesses form a bore 78. At the rearward end of the articulating jaws 74a, 74b are opposing, mutually facing cam surfaces 80a, 80b. The function and purpose of the cam surfaces 80a, 80b will more fully explained below.

The body member 72 further comprises a set of rearwardly projecting outer legs 82. A resilient second set of rearwardly projecting legs 84 is located interiorly of the first set of legs 82. Each resilient inner leg 84 includes an inwardly facing flange 86 formed thereon. The resilient inner legs 84 are provided with a cantilevered pin 90 engaging a recess 91 in each jaw 74a, 74b. When the jaws 74a, 74b are closed, as in FIG. 8B, the pin 90 is situated in a rear position in the recess 91, that is, in a direction towards the holder, and when the jaws are opened, as in FIG. 8A, the pin is situated in a forward position, in which the pin is limiting the horizontal opening angle of the jaws.

In FIG. 9 the arrangement for mounting the needle guide 70 onto the path determiner 20 is shown. A lower holder attachment piece 100 is integrally formed with the path determiner 20. The attachment piece 100 comprises two outer, parallel grooves or locking members 102 extending between the front and rear faces of the path determiner 20. The inner legs 84 of the needle guide 70 are pushed into the grooves 102. The resilient legs 84 deflect outwardly as the needle guide 70 is pushed onto the attachment piece 100. As can be seen in FIG. 5, when the inwardly directed flanges 86 clear the rear face of the attachment piece 100, the resilient legs 84 snap inwardly, and the flanges 86 engage the rear part of the attachment piece to prevent the needle guide 70 from becoming disengaged. The length of the resilient legs 84 is such that the flanges 86 engage the end wall of the bottom walls of the locking grooves 102 on the rear side of the attachment piece 100.

Figures 10A, 10B:
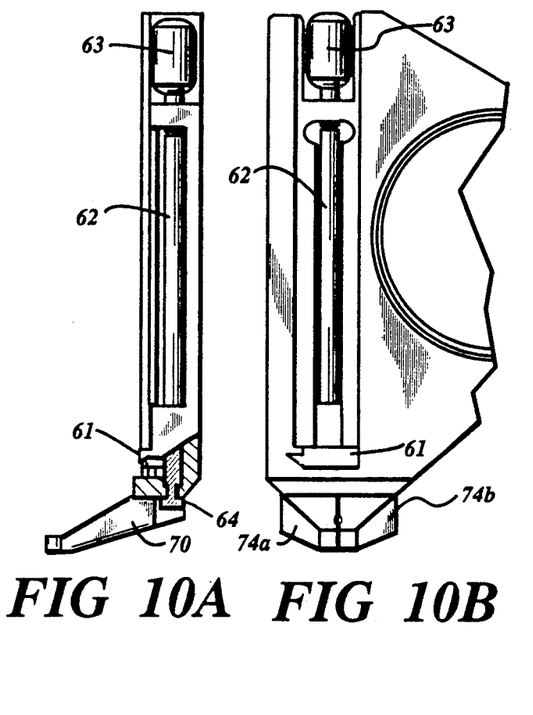
FIGS. 10A-C are side, front, and top views, respectively, of the needle guide and path determiner showing the jaws of the needle guide in the closed position.
Figure 10C:
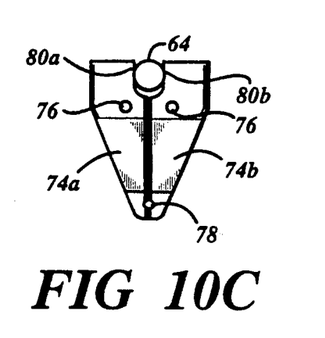
Figure 11A:
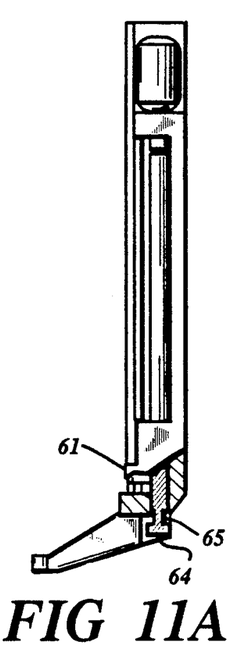
FIGS. 11A-C are side, front, and top views, respectively, of the needle guide and path determiner showing the jaws of the needle guide in the opened position.
Figure 11B:
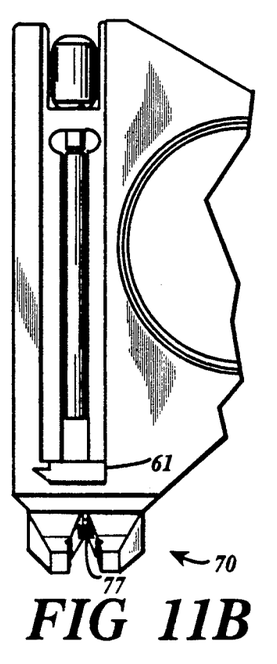
Figure 11C:
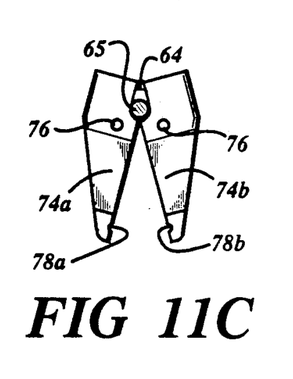

FIGS. 10 and 11 depict a mechanism whereby the jaws 74a, 74b of the needle guide 70 are automatically opened. With the needle guide 70 mounted to the lower end of the path determiner 20, and with the screw 62 in its normal upwardly biased position as shown in FIGS. 10A–C, the cam surfaces 80a, 80b bear against the enlarged flange 64, and the rear portions of the articulating jaws 74a, 74b are biased apart against the force of the spring 77. The forward portions of the jaws 74a, 74b are thus biased together, with the cooperatively aligned semicircular recesses 78a, 78b forming the bore 78. When the screw 62 is displaced axially downward, as shown in FIG. 11A–C, the reduced annular recess portion 65 of the screw is brought into correspondence with the cam surfaces 80a, 80b of the jaws 74a, 74b. The annular recess does not bias the cam surfaces apart as widely as the disc-shaped flange 64, and the forward portions of the jaws 74a, 74b are therefore able to be biased apart by the spring 77, thereby causing the jaws of the needle guide 70 to open.

Referring again to FIG. 3, a sleeve 106 has a tapered central opening 108 and a pair of outwardly extending flanges 109 which slidingly mate in a dove-tail manner with the groove 60 of the path determiner 20. A spring-propelled tissue sampling device 110 is received within the central opening 108 of the sleeve 106. In the disclosed embodiment, the tissue sampling device 110 is a device of the type marketed under the MONOPTY ® trademark by the Urological Division of C. R. Bard, Inc., Covington, Ga., U.S.A. The tissue sampling device 110 comprises a biopsy needle 112 and a housing 114 of known construction and having a spring-propelled needle driving mechanism housed therein. The central opening 108 of the sleeve 106 is correspondingly tapered to conform to the tapered housing of the tissue sampling device 110. By the sliding engagement of the flanges 109 with the groove 60 of the path determiner 20, the tissue sampling device 110 is slidably mounted to the path determiner for movement along a path defined by the groove.

Referring now to FIG. 7, with the tissue sampling instrument 110 thus slidably mounted to the path determiner 20, the needle 112 of the tissue sampling device is inserted through the bore 78 of the needle guide 70 at the lower end of the path determiner. The lowermost extent of travel of the sleeve 106 in the groove 60 on the path determiner 20, and thus the penetration depth of the needle 112, is determined when the sleeve 106 abuts the shelf 61. Thus, the depth of penetration of the needle 112 is limited by the location of the shelf 61 which, in turn, is adjustable by rotating the knob 63 at the upper end of the screw 62.

Referring again to FIG. 6, the puncture guidance device 10 further comprises a means for capturing and retaining the sleeve 106 to prevent recoil once the tissue sampling device 110 has reached the lower extent of its travel. The shelf 61 is provided with an upstanding, resilient cantilever pin 120 having an enlarged head or boss 122. The sleeve 106 is at its lower part provided with a protrusion 125 sized to fit into the space between the bottom surface 126 of the shelf 61 and the enlarged boss 122 of the pin 120. When the sleeve 106 reaches the bottom of the groove 60 and engages the shelf 61, the protrusion 125 snaps into the space between the shelf and the enlarged boss 122 of the pin 120. The sleeve 106 thus locks onto the shelf 61, preventing the sleeve from rebounding upwardly and thus eliminating puncture recoil of the biopsy needle.

Figure 12:
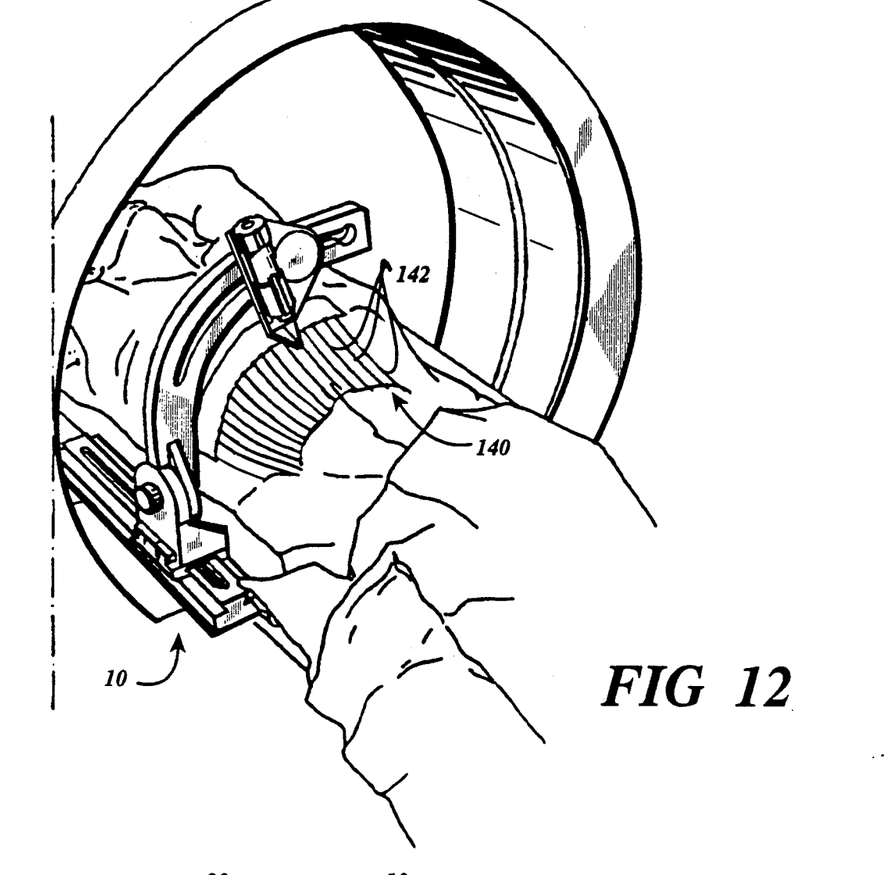
FIG. 12 is a perspective view of the puncture guidance device of FIG. 1 mounted to a patient table of a computer tomograph with a patient lying on his back on the patient table.

In FIG. 12, the puncture guidance device 10 according to the present invention is shown in position over a patient lying on his back. Positioned on the patient's body is an indication device 140 comprising several parallel X-ray dense markers 142 spaced a uniform distance from one other and oriented substantially perpendicular to the computer tomographical section plane, that is, substantially parallel to the longitudinal axis of the patient.

Figure 13:
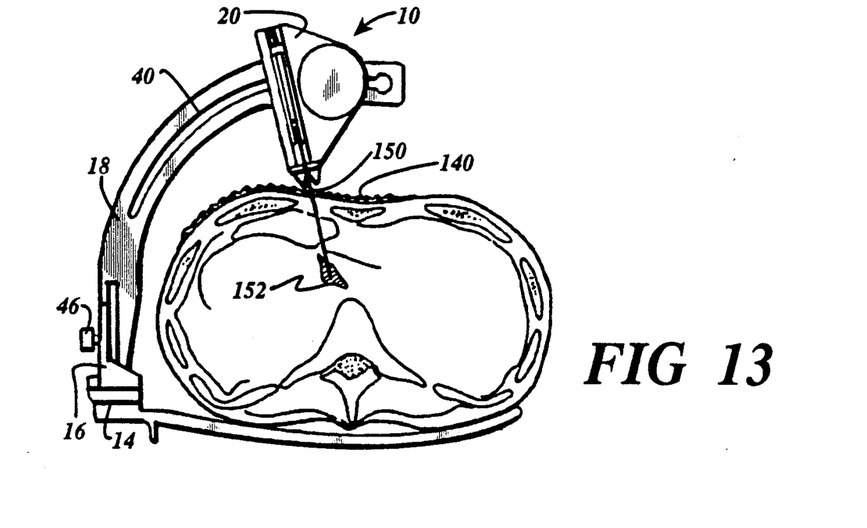
FIG. 13 is an axial plane view transverse to the longitudinal axis of a patient showing the puncture guidance device of FIG. 1 directing the needle of a tissue sampling instrument to a target location within the body of the patient.
Figure 14:
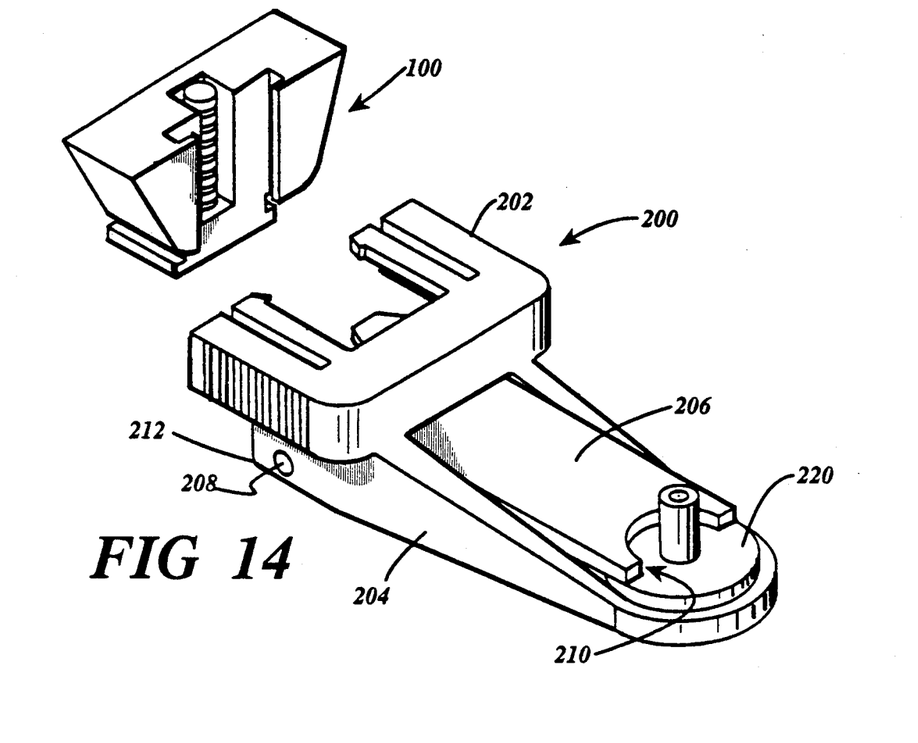
FIG. 14 is a perspective view of an alternate embodiment of a needle guide for use with the puncture guidance device of FIG. 1.
Figure 15:
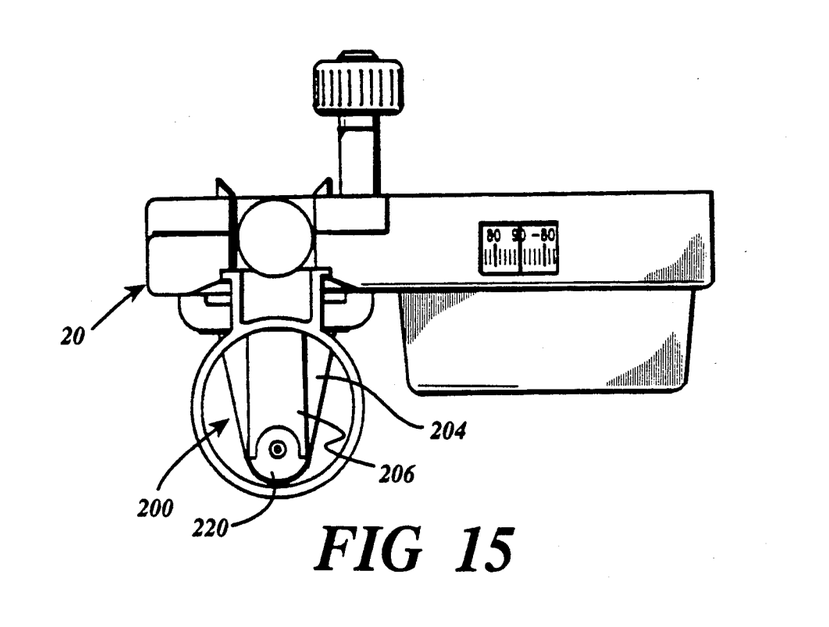
FIG. 15 is a top view of the path determiner showing the needle guide of FIG. 14 mounted thereto.

FIG. 13 shows a computer tomographical section of the patient with adhered indication device 140 in combination with the puncture device 10 according to the invention. Here the needle 112 is inserted between the markers 142 in the indication device 140 into the body of the patient at a puncture location 150. The tip of the needle is disposed within a target tissue 152 in the patient's body.

The operation of the puncture guidance device 10 to retrieve a tissue specimen will now be described. While the operation will be explained with specific reference to a suspected pathological change located with computer tomography, it will be understood that the apparatus is not necessarily limited to use with computer tomography but can be used with any appropriate imaging technology.

The base 12 of the puncture guidance device 10 is mounted to the patient table 22 of the computer tomograph, and the patient is positioned on the concave back plate 24. The indication device 140, comprising several parallel X-ray opaque markers 142 uniformly spaced from one other and substantially perpendicular to the computer tomographical section plane, is positioned, and preferably adhered, on the upper surface of the patient's body in the manner depicted in FIG. 12. The patient table 22 is then introduced into the computer tomograph. At this stage of the procedure, the support arm 18 and path determiner 20 are typically not mounted to the base 12.

One or more computer tomographical section views are taken, and the CT image is reviewed to look for any suspected pathological changes. When a suspected pathological change has been located, the puncture direction and depth to the target tissue 152 are measured directly on the CT image. The point at which the puncture line intersects the patient's skin identifies the entry point or puncture location 150. The image plane of the CT scan image is identified on the patient's body with a light plane or light line associated with the CT scan device. This plane thus identifies the plane within which the tissue sample is to be retrieved. The radiopaque marking device 140 is visible on the CT image, and the markers 142 adjacent the entry point 150 are identified on the CT image. The markers 142 on the patient's body corresponding to the markers on the CT image adjacent the optimum entry point 150 are then identified. The entry point 150 on the patient's body is localized in the image plane identified with the light line associated with the CT scan device, and within that image plane the entry point is further localized by reference to the radiopaque markers 142 on the patient's body. The desired puncture location 150 is marked on the patient's skin, such as with a color pen.

Once the puncture location 150 has been localized on the patient's body, the support arm 18 and path determiner 20 are mounted to the carriage 16 in the manner hereinbefore described. The locking pin 38 on the carriage 16 is pivoted to rotate the recess 39 into alignment with the upper surface 30 of the track 14 so that the carriage 16 is freely displaceable along the length of the track. The carriage 16 is moved along the track 14 until the needle guide 70 of the path determiner 20 lies in the image plane. The locking pin 38 is then pivoted to rotate the recess 39 away from the upper surface 30 of the track 14 to bring the shank of the locking pin into interfering engagement with the upper surface of the track, thereby locking the carriage 16 with respect to the track. The puncture guidance device 10 is now properly adjusted in the horizontal plane.

The path determiner 20 is next adjusted to provide proper positioning of the puncture guidance device 10 in the vertical plane. With the knob 56 loosened to permit the path determiner 20 to move freely within the guide slot 40, the path determiner is adjusted with respect to the support arm 18. The location of the path determiner 20 on the support arm 18 is adjusted until the path determiner is generally aligned with the desired puncture location 150 marked on the patient's body. The angle of the path determiner 20 is set by sighting through the bore 78 of the needle guide 70 at the puncture location 150 while simultaneously observing the angle meter 66 and adjusting the path determiner on the support arm 18 until the bore is aligned with the puncture location and the angle indicated by the angle meter corresponds to the desired puncture angle as determined from the computer tomographic image. The height of the path determiner 20 is then adjusted by sliding the path determiner vertically on the mounting bolt 50 until the lower surface of the needle guide 70 rests on the patient's skin. With these adjustments complete, the knob 56 is tightened to fix the path determiner 20 with respect to the support arm 18.

With the path determiner 20 thus positioned and fixed on the support arm 18, the puncture depth as measured from the CT image is now set. The shelf 61 is adjusted with respect to the elongated groove 60 by rotating the knob 63 at the upper end of the screw 62. As the screw 62 is rotated, the threaded engagement between the shelf 61 and screw moves the shelf along the groove 60. The appropriate scale 68a or 68b is selected, depending upon the length of the biopsy needle in the tissue sampling device. The shelf 61 is adjusted upwardly or downwardly within the groove 60 by rotating the knob 63 at the upper end of the screw 62 until the upper surface of the shelf is aligned with the marking on the appropriate scale 68a or 68b which marking corresponds to the desired depth of penetration as measured from the CT image, for example 50 mm.

With the path determiner 20 thus aligned and the depth of penetration thus set, the sleeve 106 with the energized tissue sampling device 110 received therein is inserted into the upper end of the groove 60. The screw 62 is in its normal position as shown in FIGS. 10A-C, that is, the screw is spring biased upwardly to the upper extent of its limited range of axial movement. The cam surfaces 78a, 78b of the jaws 74a, 74b of the needle guide 70 are thus biased apart by the disc-shaped flange 64 at the lower end of the screw 62. The forward ends of the jaws 74a, 74b are thus biased together such that the cooperating semicircular recesses 78a, 78b form the bore 78. The needle 112 of the tissue sampling device 110 is directed through the bore 78 of the needle guide 70 and thereby to the desired puncture location 150.

To effect a puncture, the tissue sampling device 110 and sleeve 106 are driven downwardly, puncturing the patient's skin with the needle 112 of the tissue sampling device. During the puncture, the needle 112 is partly guided by the sleeve 106 riding in the groove 60 of the path determiner 20 and partly by the bore 78 of the needle guide 70. When the needle 112 has reached the predetermined depth of penetration, the sleeve 106 impinges upon the shelf 61, preventing further movement. As the sleeve engages the shelf, two things happen. First, the protrusion 125 on the sleeve 106 snaps into the space between the shelf 61 and the the enlarged boss 122 of the pin 120 as shown in FIG. 6, thereby locking the sleeve 106 onto the shelf 61 and preventing the tissue sampling instrument 110 from recoiling upwardly. Second, the downward force on the shelf 61 displaces the screw 60 axially downward to the position shown in FIGS. 11A-C, disengaging the flange 64 on the lower end of the screw from the cam surfaces 78a, 78b of the jaws 74a, 74b of the needle guide 70, and bringing the annular recess portion 65 of the screw into correspondence with the cam surfaces of the jaws. With the disc-shaped flange 64 no longer forcing the forward ends of the jaws 74a, 74b together, the spring 77 biases the jaws apart, thereby disengaging the needle guide 70 from the needle 112. In this position, the needle 112 is no longer retained within the bore 78 of the needle guide 70 and is thus somewhat movable, thus enabling the patient to breathe more easily and to move without pain. The patient advantageously remains in the same breathing position for taking of the picture and the puncture. After inserting the needle 112, the position of the needle tip is confirmed by taking another computer tomographical picture. To take another CT image, the patient table is moved into the CT apparatus with the support arm 18 and path determiner 20 still mounted to the base 12 and with the needle 112 of the tissue sampling instrument 110 still within the patient's body. If the needle tip is in the correct position with respect to the target tissue, as shown in FIG. 13, the puncture is completed by activating the tissue sampling device 110 in the conventional manner while the patient is still within the computer tomograph. As the tissue sampling device 110 is activated, the needle 112 is shot into the target tissue, capturing a tissue specimen within a notch adjacent the forward end of the needle. Successful sampling can be confirmed from section views. After the patient has been brought out of the computer tomograph, the needle holding the tissue sample is taken out of the patient, and the procedure is completed.

Occasionally, the target tissue or target organ may be located in a position which makes access impossible in an axial plane, that is, in a plane normal to the longitudinal axis of the patient. For example, the target tissue or target organ may be located directly underneath a rib or other bone or organ. In such an instance, the skin entry point and the target tissue are not in the same axial slice, and the optimum needle path will lie in a plane which is oblique to the longitudinal axis of the patient. To accommodate a needle path in a plane which is oblique to the longitudinal axis of the patient, the patient table can be tilted with respect to the CT imaging apparatus until a plane is identified which is free from obstruction. The support arm 18 can then be pivoted about a horizontal axis by loosening the knob 46 and adjusting the angular orientation of the support arm to match the image plane of the CT imaging apparatus. Thus, the plane of the needle path, while oblique, nonetheless corresponds to the image plane visualized on the CT image.

The needle guide of the disclosed embodiment is characterized by jaws which pivot in a generally horizontal plane. In certain cases, however, obstacles may prevent horizontal articulation of the jaws Also, jaws which open along the surface of the skin may obstruct access to the needle penetration site. Furthermore, opening of the needle guide during a heavily angled puncture may result in forcing the lower jaw into the patient's skin. To overcome these problems, an alternate embodiment of a needle guide 200 is disclosed which incorporates vertically articulating jaws.

In FIGS. 14-17, the construction of the needle guide 200 of the alternate embodiment is shown. The needle guide 200 comprises a body 202, a first or lower jaw 204, and a second or upper jaw 206. The body 202 includes appropriate flange means for mounting the needle guide 200 to the lower end of the path determiner in the same manner as hereinabove described with respect to the needle guide 70 of the preferred embodiment.

Figure 16:
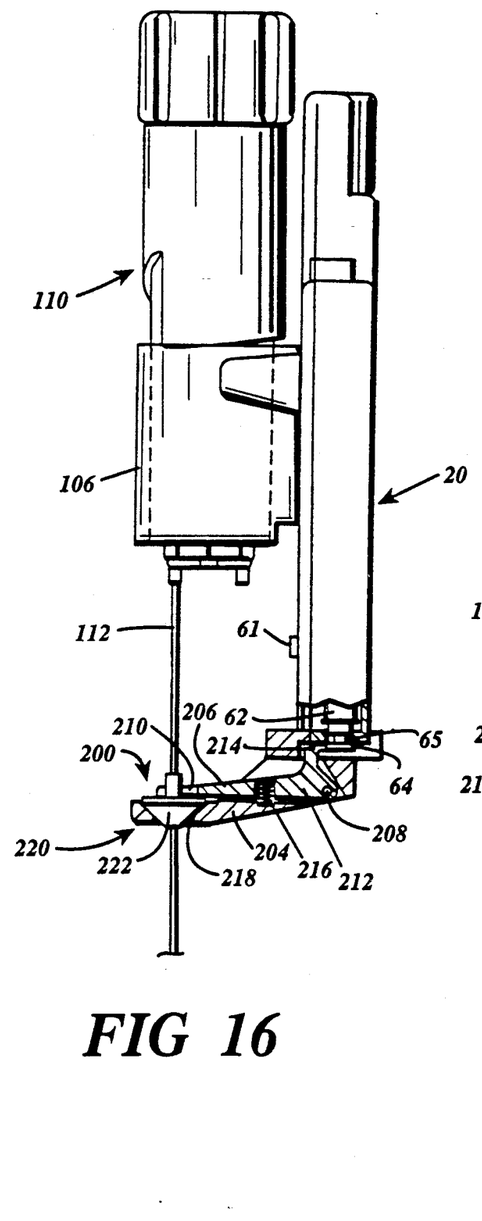
FIG. 16 is a side view of the path determiner with tissue sampling device mounted thereto and having the needle guide of FIG. 14 mounted thereto, the jaws of the needle guide being in the closed position, and the needle guide being cut away to reveal interior detail.
Figure 17:
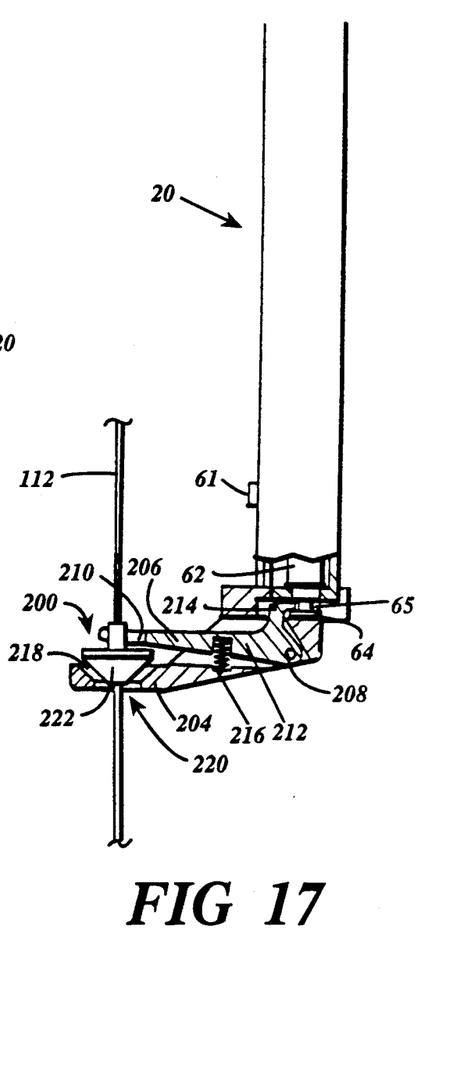
FIG. 17 is a side view of the structure of FIG. 16 with the jaws of the needle guide being in the open position.

Referring especially to FIGS. 16 and 17, the upper jaw 206 of the needle guide 200 is pivotably mounted to the body 202 on a horizontal pin 208 for articulation in a generally vertical plane. The upper jaw 206 comprises a U-shaped forward recess 210, a rear heel 212, and a hook-shaped portion 214 extending upward and rearward. The upper jaw 206 is spring biased in an upper direction by a spring 216 located within a recess in the lower jaw 202.

The lower jaw 204 projects forwardly from the body 202 and is fixed with respect thereto. The lower jaw 202 comprises a conical recess 218 into which a sterile guide bushing 220 is received. The guide bushing 220 comprises a conical body portion 222 and a bore for receiving the needle of the tissue sampling instrument. The diameter of the bore may be dimensioned to accommodate different needle gauges. The guide bushing 220 is pushed vertically downward into the conical recess 218 by the upper jaw 206, and thus the U-shaped recess 210 is positioned about the bushing.

In the position shown in FIG. 16, the jaws 204, 206 are closed. In this position, the hook-shaped portion 214 of the jaw 206 is abutting against the edge of the disc-shaped flange 64 of the screw 62 in the path determiner 20. The screw 62 is spring biased in an upward direction. This position is employed during the penetration of the needle 212 towards the pathologically changed organ. In FIG. 17, the disc-shaped flange 64 of the screw 62 has been brought to the lower most position, and the hook-shaped portion 214 of the jaw 206 engages the annular recess 65 of the screw 62 located above the disc-shaped flange 64. Since the U-shaped recess 210 of the jaw 206 now has been displaced upwardly, the conical portion 222 of the guide busing 220 is no longer retained within the recess 218, and thus the needle 212 positioned within the guiding bushing 220 is no longer fixed in its position. When the needle guide 200 is released in this manner, it becomes easier for the patient to breathe and move without pain during the subsequent imaging to check that the needle position is correct. According to the alternate embodiment, the jaw 206 is upwardly pivotable such that the jaws separate in a vertical plane, and thus no extra space is required in the horizontal plane.

As will be appreciated from the foregoing description, the pair of vertical scales 68a, 68b located on the path determiner 20 are calibrated according to the length of the needle 112 of the tissue sampling instrument 110. The path determiner 20 depicted in FIG. 4 is intended for use with biopsy instruments having needles of either 120 mm or 160 mm in length. Thus, in the disclosed embodiment, the "zero" point of the scale 68b is 40 mm higher than the "zero" point of the scale 68a.

However, it will be appreciated that it may be desired to use a tissue sampling instrument having a needle of a length other than 120 mm or 160 mm, or that it may be desired to use an instrument other than a tissue sampling instrument with the guidance device 10. In such an instance, it would be advantageous to accommodate scales other than the two scales 68a, 68b. Furthermore, whenever there is more than one scale on the path determiner 20, there is always the possibility of the user accidentally referencing the wrong scale and thus setting the shelf to the wrong penetration depth. Thus, it would be desirable to provide a means for removably mounting a scale on the path determiner, thereby to accommodate a variety of scales and to permit only the scale needed for a particular application to be placed on the path determiner.

To provide such an arrangement, a vertical slot can be provided in the front face of the path determiner 20 adjacent the groove 60. A scale having the desired calibration can then be inserted into the slot. When it is desired to use a different instrument requiring a different scale, the first scale is removed from the slot and replaced with a different scale having a different calibration. This arrangement not only permits a variety of scales of differing calibrations to be used with the path determiner but also accommodates only a single scale at a time, thereby preventing the possibility inherent with multiple scales that the user may accidentally reference the wrong scale and thereby misset the puncture depth.

The puncture device and the method according to the present invention provide maximum use of computer tomographically derived punctures both as regards economy in association therewith and comfort for the patient. Furthermore, it gives great precision enabling samples to be taken from very small pathological changes, the method is simple and safe allowing a great number of samplings to be made per time unit, and as a result of the obtained verification the method is very reliable.

One feature of the disclosed embodiment is the use of a track 14 having a curved upper track surface 30. During the use of early puncture guidance devices, the track construction gave rise to substantial artefacts on the computer tomographical picture in the form of interfering zones of lines emanating from the top of the track. These artefacts made the localization of the target tissue for the biopsy sampling more difficult. It was found that the flat upper track surface, and not the sharp angles of the corners of the track, was the cause of the artefacts. The advantage of the curved rather than flat upper track surface 30 is that it thus eliminates or substantially reduces artifacts on the CT image.

In the disclosed embodiment the carriage 16 is locked in position on the track 14 in the horizontal plane by a locking pin 38. However, it will be appreciated that alternate methods for positioning the carriage on the track may be used. For example, the carriage and track can be configured to provide a sufficient frictional engagement that the carriage can be displaced by hand on the track yet be retained in the desired position without a locking pin. Alternatively, the track can be configured with a screw which runs the length of the track and threadingly engages the carriage such that the carriage is driven along the track when the screw is turned and is fixed in place when the screw is stationary.

The present invention has been disclosed with respect to a puncture guidance device 10 having a removable needle guide 70. This arrangment is believed particularly advantageous in a number of respects. First, the inexpensive construction of the needle guide 70 makes it economically feasible to use a new sterile needle guide with each procedure. Thus, there is no need to sterilize the needle guide, since a contaminated needle guide is simply discarded and replaced with a new, sterile needle guide. Furthermore, where a needle guide having a smaller or larger diameter aperture is needed, such as for example when using the apparatus as a drill guide for drilling a hole in a bone, the standard needle guide configuration can be replaced with a needle guide having an appropriately sized aperture.

However, notwithstanding these advantages, it will be understood that the present invention is not limited to a puncture guidance device having a removable needle guide. The puncture guidance device will be just as functional, though perhaps less convenient to maintain, if the needle guide is fixedly mounted to the lower end of the path determiner. In such an instance, it may be desirable to provide the puncture guide with a larger aperture, within which may be positioned a sterile bushing, for example a short length of sterile surgical tubing. The needle of the tissue sampling device would thus be directed through the sterile bushing, and the bushing would be discarded after each use and replaced with a fresh sterile bushing.

The preferred embodiment has been disclosed with respect to a puncture guiding device especially adapted for use with the MONOPTY ® biopsy instrument marketed by the Urological Division of C. R. Bard, Inc. This instrument provides the particular advantage that its largely plastic construction permits it to be introduced into the tomograph for verifying the location of the needle without causing excessive artefacts on the CT image. However, it will be understood that other types of biopsy instruments may be used without departing from the scope of the invention.

Furthermore, while the preferred embodiment has been disclosed with respect to a guiding apparatus especially adapted for use with a tissue sampling apparatus, it will be appreciated that the apparatus can be adapted to a variety of other uses, including, without limitation, guiding a needle, a drill or any other instrument for puncturing or penetrating an organ, bone, or tissues of a patient.

Finally, it will be understood that the foregoing embodiments have been disclosed by way of example, and that other modifications may occur to those skilled in the art without departing from the scope and spirit of the appended claims.

What is claimed is:

1. An apparatus for guiding a puncture instrument through an entry point in the body of a patient to a target location within said body of said patient, comprising:
    support means for establishing a fixed reference point adjacent to said body of said patient;
    path determining means mounted to said support means and adjustable to define a path through said entry point in a predetermined direction;
    instrument holding means mounted to said path determining means and slidably movable with respect thereto along said path defined by said path determining means for holding a puncture instrument and for moving said puncture instrument along said path defined by said path determining means; and
    depth determining means operatively associated with said path determining means for limiting the extent of said movement of said puncture instrument along said path, whereby said puncture instrument penetrates the patient's body to a predetermined depth.

2. The apparatus of claim 1, further comprising instrument guide means operatively associated with said path determining means for guiding said puncture instrument as said puncture instrument is moved along said path defined by said path determining means.

3. The apparatus of claim 2, wherein said instrument guide means automatically disengages from said puncture instrument when said depth determining means limits said extent of said movement of said puncture instrument.

4. The apparatus of claim 3, wherein said instrument guide means comprises a pair of cooperating jaws mounted to said path determining means and which disengage from said puncture instrument when said depth determining means limits said extent of said movement of said puncture instrument.

5. The apparatus of claim 4, wherein said pair of cooperating jaws are pivotably mounted to said path determining means for articulation in a horizontal plane, and wherein both of said jaws pivotably disengage from said puncture instrument when said depth determining means limits said extent of said movement of said puncture instrument.

6. The apparatus of claim 4, wherein one of said pair of cooperating jaws is pivotably mounted to said path determining means for articulation in a horizontal plane, and wherein said one of said pair of cooperating jaws pivotably disengages from said puncture instrument when said depth determining means limits said extent of said movement of said puncture instrument.

7. The apparatus of claim 2, wherein said instrument guide means is removably mounted to said path determining means.

8. The apparatus of claim 1, further comprising recoil suppression means operatively associated with said depth determining means for capturing said puncture instrument when said depth determining means limits said extent of said movement of said puncture instrument to prevent said puncture instrument from recoiling.

9. The apparatus of claim 1, wherein said patient lies on a support surface, and wherein said support means for establishing a fixed reference point adjacent to said body of said patient comprises:
 a track mounted to said support surface;
 a carriage movably mounted to said track; and
 a support arm mounted to said carriage, said path determining means being mounted to said support arm.

10. The apparatus of claim 9, wherein said track comprises a curved upper surface for minimizing artifacts when said apparatus is used in conjunction with imaging technology.

11. The apparatus of claim 9, wherein said support arm is pivotably mounted to said carriage about a horizontal axis of rotation such that said support arm can be angularly adjusted with respect to said carriage.

12. The apparatus of claim 1, wherein said target location within said body of said patient is identified by means of imaging technology, wherein said predetermined direction and said predetermined depth are computed from an image obtained by said imaging technology, and wherein said path determining means further comprises an angle indication means for indicating the angle of said path determining means, whereby said path determining means can be aligned along said predetermined direction by reference to said angle indication means to direct said puncture instrument to a location identified on said image.

13. The apparatus of claim 1, further comprising at least one scale located on said path determining means and calibrated with respect to said puncture instrument for indicating a depth to which said puncture instrument will penetrate the body of said patient, whereby said depth determining means can be aligned with a desired location on said scale to determine said predetermined depth to which said puncture instrument will penetrate said body of said patient.

14. The apparatus of claim 13, further comprising means for removably mounting said scale to said path determining means to accommodate a variety of said scales calibrated to a variety of puncture instruments.

15. The apparatus of claim 14, wherein said means for removably mounting said scale to said path determining means comprises channel means formed on said path determining means for slidably receiving a scale therewithin.

16. The apparatus of claim 1, wherein said path defined by said path determining means comprises a slot means, and wherein said instrument holding means comprises a sleeve for holding said puncture instrument, said sleeve having flange means for slidably engaging said slot means for moving said puncture instrument along said path defined by said path determining means.

17. The apparatus of claim 16, wherein said depth determining means operatively associated with said path determining means for limiting the extent of said movement of said puncture instrument along said path comprises a shelf operatively associated with said slot means and movable along said slot means, said sleeve abutting said slot means to limit the extent of movement of said puncture instrument along said slot means.

18. The apparatus of claim 17, further comprising recoil suppression means operatively associated with said shelf and said sleeve for locking said sleeve to said shelf when said sleeve abuts said shelf, thereby to prevent said puncture instrument from recoiling.

19. A method for retrieving a tissue specimen from the body of a patient using a puncture guidance device comprising a path determining means mounted to a support means and angularly adjustable with respect thereto, and an instrument holding means mounted to said path determining means and slidably movable with respect thereto such that the needle of a biopsy instrument mounted to said path determining means will follow a path defined by said path determining means as said instrument holding means slides with respect to said path determining means, said instrument holding means having a length of travel with respect to said path determining means which is adjustable by a user, said method comprising the steps of:
 placing a marking device comprising a plurality of parallel, spaced-apart X-ray opaque markers on the body of the patient such that the marking device lies generally in the plane within which an image is to be taken and such that the markers are disposed perpendicularly to the plane within which said image is to be taken;
 taking an image of the patient in an image plane using suitable imaging technology;
 identifying a target location within the body of the patient from said image;
 identifying from said image an optimum line of penetration from outside the patient's body to said target location within the patient's body;
 identifying on said image an entry location at which said line of penetration intersects the patient's skin;
 identifying the X-ray opaque markers on said image adjacent said entry location;
 identifying the image plane on the patient's body corresponding to the plane of said image;
 identifying the X-ray opaque markers on the patient's body corresponding to the identified markers adjacent said entry location;

locating the entry location on the patient's body in the identified image plane and between the identified X-ray opaque markers;

measuring the angle and depth of penetration on said image along said optimum line of penetration to said target location within the patient's body;

aligning said path determining means of said puncture guidance device such that said path defined by said path determining means corresponds to said measured angle of said optimum line of penetration; and adjusting said length of travel of said instrument holding means with respect to said path determining means such that a needle tip of a biopsy instrument mounted to said instrument holding means will penetrate to said measured depth of penetration to said target location;

whereby when said instrument holding means is slidably advanced with respect to said path determining means, the needle tip of a biopsy instrument mounted to said instrument holding means will travel along a path intersecting said target location to a depth corresponding to said target location to position said needle tip for retrieving a biopsy specimen from said target location.

20. The method of claim 19, wherein said guidance device includes a bore for guiding a needle along said line of needle travel and further comprises an angle meter for indicating the angle of said line of needle travel, and wherein said step of setting a puncture guidance device to guide a needle at said measured angle through said entry location on the patient's body comprises the steps of:

sighting through said bore in said guidance device to align said bore with said entry location; and while maintaining said bore aligned with said entry location, adjusting said guidance device until said angle meter indicates said line of needle travel to be at an angle corresponding to the angle of said optimum line of penetration as measured on said image.

21. An apparatus for mounting a tissue sampling instrument to a guidance device, said guidance device having a slot means defining a path of travel, and said apparatus comprising:

sleeve means for receiving a tissue sampling instrument therein such that said instrument is retained within said sleeve means; and flange means operatively associated with said sleeve means for slidably engaging said slot means in said guidance device, said apparatus thereby being slidably mounted to said guidance device to guide said tissue sampling instrument along said path of travel.

22. The apparatus of claim 21, wherein said sleeve means is configured such that said instrument is retained within said sleeve means by an interference fit between said sleeve means and said instrument.

* * * * *